United States Patent [19]

Schmidt

[11] 4,044,265

[45] Aug. 23, 1977

[54] MOBILE CHAIR FOR PANORAMIC DENTAL X-RAY MACHINE

[75] Inventor: Walter A. Schmidt, Milwaukee, Wis.

[73] Assignee: General Electric Company, Schenectady, N.Y.

[21] Appl. No.: 664,162

[22] Filed: Mar. 5, 1976

[51] Int. Cl.² .................. G01N 21/00; H01J 37/20
[52] U.S. Cl. ........................ 250/439 P; 250/446; 250/491
[58] Field of Search ............... 250/439 P, 446, 448, 250/456, 490, 491; 128/377

[56] References Cited

U.S. PATENT DOCUMENTS

| | | | |
|---|---|---|---|
| 1,442,027 | 1/1923 | Levenson | 250/456 |
| 2,798,958 | 7/1957 | Hudson et al. | 250/490 |
| 2,962,589 | 11/1960 | Dlouhy et al. | 250/456 |
| 3,506,826 | 4/1970 | Kosters | 250/446 |
| 3,585,386 | 6/1971 | Horton | 250/491 |
| 3,636,349 | 1/1972 | Faude | 250/439 P |
| 3,655,968 | 4/1972 | Moore et al. | 250/448 |
| 3,803,418 | 4/1974 | Holstrom | 250/491 |

*Primary Examiner*—Alfred E. Smith
*Assistant Examiner*—B. C. Anderson
*Attorney, Agent, or Firm*—Ralph G. Hohenfeldt

[57] ABSTRACT

A mobile chair for a panoramic dental x-ray machine is provided with locking means for establishing the chair in proper position for radiography with a patient on it and for enabling the chair to be rolled out and away from the machine for being replaced by an ordinary wheel chair.

2 Claims, 5 Drawing Figures

U.S. Patent  Aug. 23, 1977  4,044,265
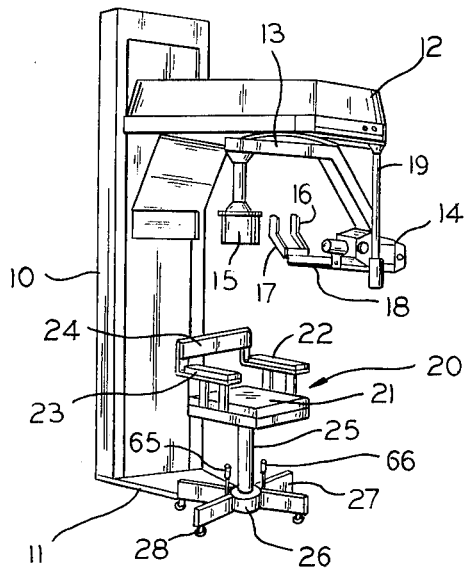
FIG.1
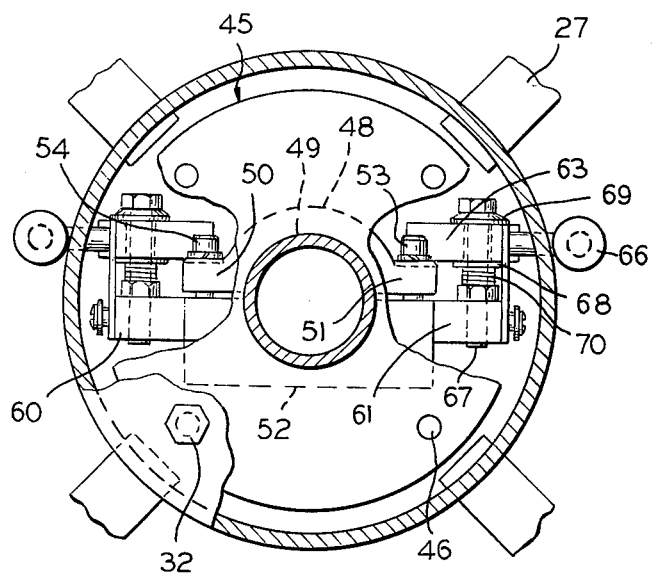
FIG.3
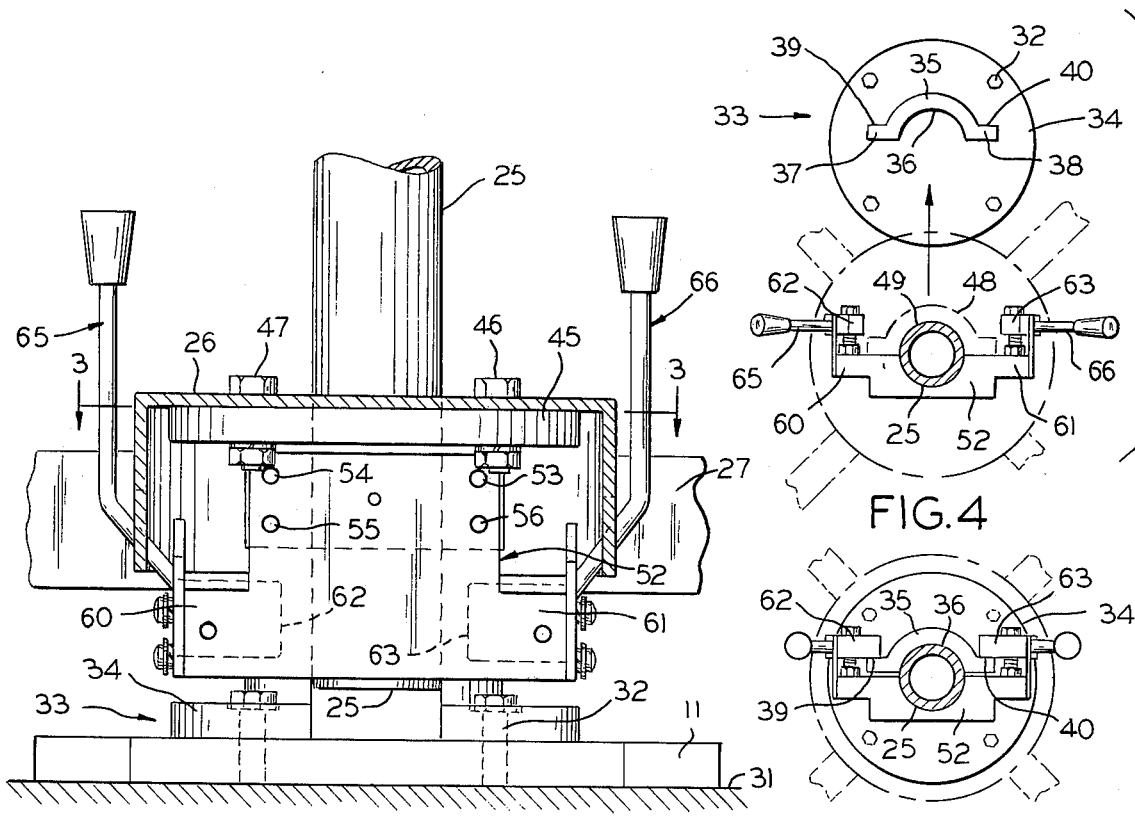
FIG.2
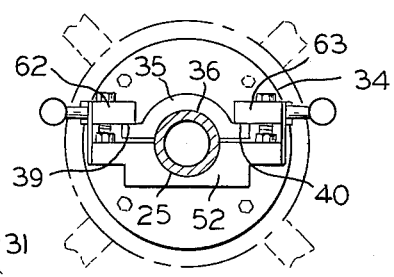
FIG.4
FIG.5

MOBILE CHAIR FOR PANORAMIC DENTAL X-RAY MACHINE

BACKGROUND OF THE INVENTION

This invention relates to a chair which is normally in a fixed position for cooperating with a panoramic dental x-ray machine to establish a patient in proper orientation for dental radiography and which is releasable and mobile to enable a patient on an ordinary wheel chair to be similarly established.

Panoramic dental x-ray apparatus is used for radiographing the entire oral region of a patient on a single film in contrast with the traditional method of taking individual radiographs of the teeth and various oral regions for a complete oral diagnostic survey. Most healthy patients simply sit down in the chair that is associated with the x-ray apparatus and their head is steadied with a headrest after which the panoramic radiograph is taken and the patient gets up and leaves. However, panoramic x-ray apparatus is frequently used in convalescent homes where patients are brought into the dental room in an ordinary wheel chair and in hospitals where accident victims should be allowed to remain in a wheel chair. According to prior practice, panoramic x-ray apparatus had a permanently fixed chair to which a patient had to be transferred from a wheel chair. In such cases a lot of time was taken by the technician in merely getting the patient properly positioned and the patient often experienced great discomfort. The present invention is devoted to mitigating these and other problems.

SUMMARY OF THE INVENTION

General objects of the present invention are to provide a patient chair which is normally locked to the panoramic dental mobile x-ray apparatus but which is releasable and movable so that an ordinary wheel chair bearing a patient may be substituted for the mobile chair.

A further object is to provide a mobile chair that has quick acting and conveniently used clamping means for engaging and disengaging it with the panoramic dental x-ray apparatus.

How the foregoing and other more specific objects of the invention are achieved will appear in the course of the ensuing description of an illustrative embodiment of the invention taken in conjunction with the drawing.

DESCRIPTION OF THE DRAWING

FIG. 1 is a perspective view of a panoramic dental x-ray machine with the new mobile chair in its normal place;

FIG. 2 is a view of the chair locking mechanism, partly in section, with the radially extending legs of the chair and the tubular chair post shown fragmentarily;

FIG. 3 is a plan view, partly in section as viewed toward the line 3—3 in FIG. 2, with some parts being shown fragmentarily and other parts being broken away;

FIG. 4 is a diagrammatic exploded view of part of the chair locking mechanism that is on the chair and another stationary part that is on the x-ray apparatus and showing how these parts are oriented just prior to the chair being interlocked with the x-ray apparatus; and FIG. 5 is a view of the mechanism shown in FIG. 4 after the chair is interlocked with the x-ray apparatus.

DESCRIPTION OF A PREFERRED EMBODIMENT

In FIG. 1, a panoramic dental x-ray unit with which the new chair cooperates comprises a column 10, a flat base plate 11 and an overhanging housing 12 in which there is mechanism that is known and not pertinent to the present invention so it will not be described. An arm 13 is disposed under housing 12 for rotation about a vertical axis. There is an x-ray tube casing 14 at one end of the arm and a film holder 15 for accommodating a continuous radiographic film in a circular configuration. The patient's head is stabilized between upstanding members 16 and 17 of a headrest that is supported on a cross arm 18 which is, in turn, mounted on a column 19. A panoramic x-ray view of the entire oral region of the patient is taken while the patient is steadied by the headrest and is facing toward the x-ray tube casing 14 while the casing and film holder orbit around the patient's head due to rotation of arm 13 about its vertical axis.

The new concept of a releasable and removable chair which is replaceable with an ordinary wheel chair is exemplified by the chair 20 in FIG. 1.

The chair has some conventional features such as a seat 21, arm rests 22 and 23, a backrest 24 and an upstanding post 25 on which the seat is supported. The base of the chair comprises an inverted or opened bottom cup or cylinder 26 from which several legs, such as leg 27, extend. Each leg is provided with roller means such as casters 28 which allow the chair to be moved with little effort on the floor of the examination room.

One form of mechanism for engaging and disengaging the chair 20 with the panoramic dental x-ray apparatus is depicted in FIGS. 2–5 to which reference will now be made.

The locking mechanism is characterized by means on the chair, in this example, which are engageable and disengageable relative to stationary means on the dental x-ray apparatus and means for releasably locking the two means together to locate the chair in a reproducible position relative to the x-ray apparatus with minimum attention to alignment being required of the attendant.

In FIG. 2 the base plate 11 of the x-ray apparatus bears on the floor 31 of the examination room. Fastened to the base plate 11 with several screws such as 32 is a stationary member 33 which has a flange 34. As can be seen in FIG. 4, cast or otherwise fastened integrally to flange 34 is an upstanding element 35 which has a semicylindrical recess or seat 36 on its front face. Element 35 also has integral sidewise extending wings 37 and 38 which have cam engageable surfaces 39 and 40, respectively. The size and shape of the tubular post 25 which supports the chair are such that the post complements the curvature of recess 36 of the stationary flange and is seatable and unseatable in the semicylindrical recess.

Mounted to the bottom inside of open bottomed chair base cylinder 26 with several bolts such as 46 and 47 is an element having a flange 45. As can be seen particularly well in FIG. 3, extending downwardly from flange 45 is an integral semicircular element 48 that has a semicylindrical seat or recess 49 which has a contour substantially complementary to the periphery of tubular post 25 and in which post 25 seats. Element 48 also has a pair of laterally extending wings 50 and 51. Post 25 extends through open bottomed inverted cylinder 26 and seats in semicylindrical seat or recess 49. The post 25 is secured or clamped into seat 49 of curved element 48 with a clamping member 52 held to element 48 with several socket headed machine screws 53–56. When the chair is in its home position, the curved element 48 which extends downwardly from flange 45 is congruent with curved element 35 which extends upwardly from base flange 34. As can be seen in FIG. 2, post 25 is long enough so that one side of its lower end may seat in downwardly extending semicircular seat 49 and a diametrically opposite portion of the pipe may seat in the lower semicylindrical seat 36. Clamping member 52 has a pair of wings 60 and 61 on which pivotable locking cams are supported as will be explained.

From the structure thus far described it should be evident that the chair may be rolled on its casters over base 11 of the x-ray apparatus until the exposed half of post 25 which extends below the downwardly extending semicylindrical seat 49 of clamping member 48 seats in semicylindrical seat 36 of stationary winged element 35 which extends upwardly from base flange 34. When the chair and apparatus are brought together in this manner, the chair will be properly oriented or directed in respect to its vertical axis, that is, the patient will be facing into the headrest for being engaged between the upstanding head support members 16 and 17.

The means for locking the chair to the x-ray apparatus will now be described. This involves using cams to clamp the wings 37 and 38 of upstanding semicylindrical socket 35 toward wings 60 and 61, respectively, of clamping member 52 which is held to pipe 25 with socket member 48. Each wing of clamping member 52 has a cam 62 and 63, respectively, pivotally mounted on it. Each cam has a handle or operating lever 65 and 66 fastened to it. The cams 62 and 63 are wedge shaped or bevelled in the vertical direction and they are mounted for rotation about a horizontal axis constituting the axis of shafts 67 which are threaded into wings 60 and 61 of clamp 52 as can be seen particularly well in FIG. 3. Typical of both cams, cam 63 is journaled on shaft 67 and there is a washer 68 on one side of the cam and a spring type cup washer 69 on the other side. A coil spring 70 spreads the cam away from wing 67 and, as is self evident, cup washer 69 yields and affords some compressive force when the chair is locked to the x-ray apparatus.

FIG. 4 shows operating handles 65 and 66 spread outwardly so that cams 62 and 63 move in the direction of the arrow without obstruction as the chair is being moved into place over stationary flange 34. FIG. 5 shows how the cams 62 and 63 are rotated by means of the handles to effect the camming and locking action after the lower exposed portion of tubular post 25 is seated in semicylindrical seat 36 of the floor flange socket 35. In this condition, the inner bevelled surfaces of the cams are in frictional engagement with the planar surfaces 39 and 40 of the wings 37 and 38, respectively, on upwardly extending socket 35. At this time, when the exposed half of post 25 is in seat 36, all of the flat surfaces on the wings involved in clamping the chair to the x-ray machine base are in parallelism with each other and the chair has the proper rotational attitude.

Now that a particular mechanism for engaging and disengaging a mobile chair with x-ray apparatus has been described, those skilled in the art will appreciate that the concept of a mobile chair cooperating with panoramic dental x-ray apparatus can be implemented in a variety of different ways. Accordingly, although an operative embodiment of the invention has been described in considerable detail, such description is intended to be illustrative rather than limiting, for the invention may be variously embodied and is to be limited only by interpretation of the claims which follow.

I claim:

1. For use with a panoramic oral radiography apparatus including arm means rotatable about a vertical axis and film holder means supported on said arm means on one side of said axis and an x-ray source supported on said arm means on the other side of said axis for said film holder means and said source to orbit about a space for accommodating the head of a radiographic examination subject in a radiographic active position;

a chair that is adapted for being locked normally in a first position such that an examination subject seated on said chair will be located substantially in said radiographic active position and which chair is removable so that a wheel chair may be situated in its place, said chair comprising:

seat means and support means including leg means supporting said seat means and roller means supporting said leg means for enabling said chair to be moved on the floor adjacent said apparatus, one of said chair and said apparatus having first means for being engaged and disengaged, and one of said chair and said apparatus having second means for alternately engaging and disengaging said first means, such that when said means are engaged said chair will be located in correspondence with said radiographic active position and when said means are disengaged said chair may be moved as a unit on said roller means to and from other positions, said means for supporting said seat means comprising vertically disposed post means having an upper end on which said seat is supported and having a lower end, means for clamping said lower end of said post means to said support means such that a portion of said post means is exposed, means that are fixed proximate to the floor beneath said arm means, said means having a recess that is substantially complementary in shape to said exposed portion of said post means for receiving said post means, selectively operable means for locking said means for clamping and said fixed means together when said exposed portion of said post means is in said recess of said fixed means.

2. The subject matter of claim 1 including:

cam means pivotally mounted on said clamping means at respectively laterally opposite sides of said post means, said fixed means having cam engageable means on laterally opposite sides of said recess, handle means attached to said cam means respectively, said handle means being manually operable to pivot said cam means into compressive contact with said cam engageable means to thereby clamp said post means of said chair onto said fixed means.

* * * * *